United States Patent [19]

Azam et al.

[11] Patent Number: 4,732,161

[45] Date of Patent: Mar. 22, 1988

[54] DEVICE FOR TREATMENT THROUGH HYPERTHERMIA

[75] Inventors: Guy Azam, La Celle St. Cloud; Guy Convert, Vincennes; Jean M. Cosset, Villejuif; Jacques Dufour, Orsay; Jean P. Mabire, Gif sur Yvette, all of France

[73] Assignee: C.G.R. MeV, Buc, France

[21] Appl. No.: 871,287

[22] Filed: Jun. 6, 1986

[30] Foreign Application Priority Data

Jun. 7, 1985 [FR] France ............................... 85 08641

[51] Int. Cl.$^4$ ........................... A61N 1/05; A61N 1/32
[52] U.S. Cl. ................. 128/784; 128/420 A; 128/422; 128/804
[58] Field of Search ............... 128/804, 784, 420 R, 128/420 A, 421, 422, 423 R

[56] References Cited

U.S. PATENT DOCUMENTS

| 4,016,886 | 4/1977 | Doss et al. | 128/784 |
|---|---|---|---|
| 4,346,715 | 8/1982 | Gammell | 128/422 |
| 4,350,168 | 9/1982 | Chable et al. | 128/798 X |
| 4,448,198 | 5/1984 | Turner | 128/422 |

Primary Examiner—Lee S. Cohen
Attorney, Agent, or Firm—Oblon, Fisher, Spivak, McClelland & Maier

[57] ABSTRACT

The present invention concerns a device for treatment by hyperthermia, comprising unipolar probes adapted to be disposed in an area to be treated of a patient, and comprising vector tubes intended to be implanted in the said area to be treated and to contain, at each hyperthermia session the said unipolar probes.

10 Claims, 4 Drawing Figures

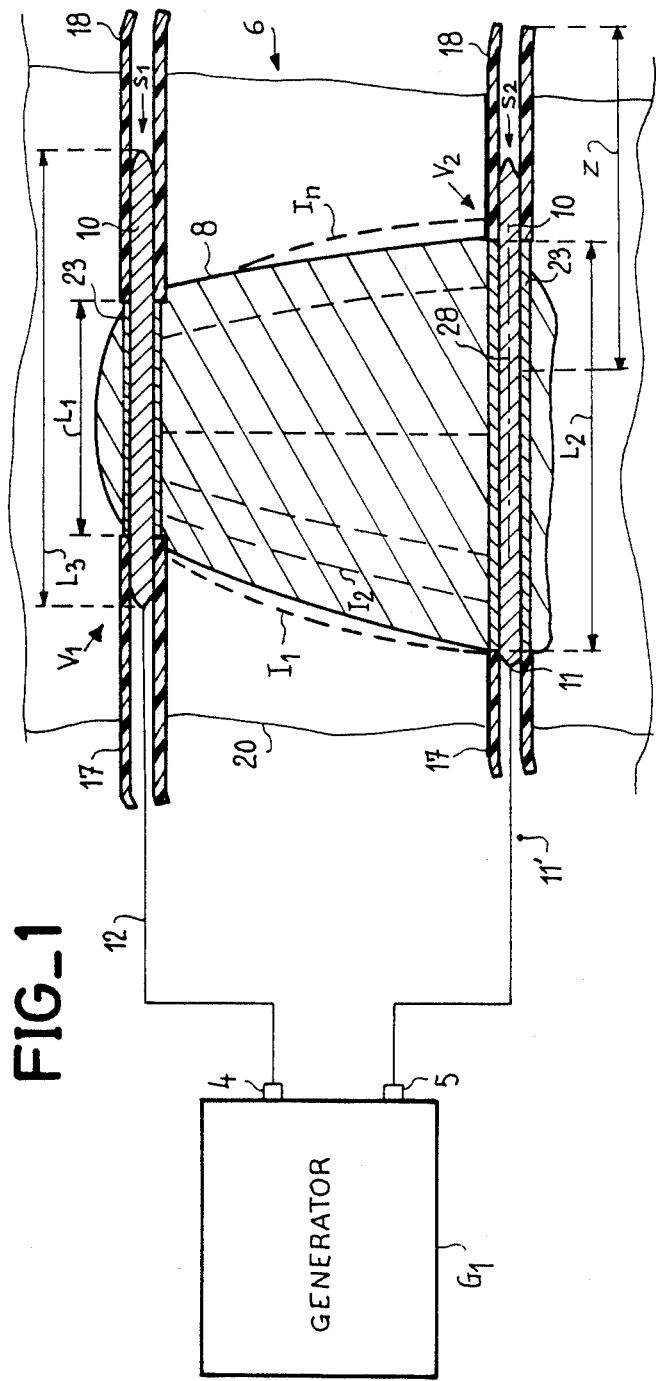
FIG_1
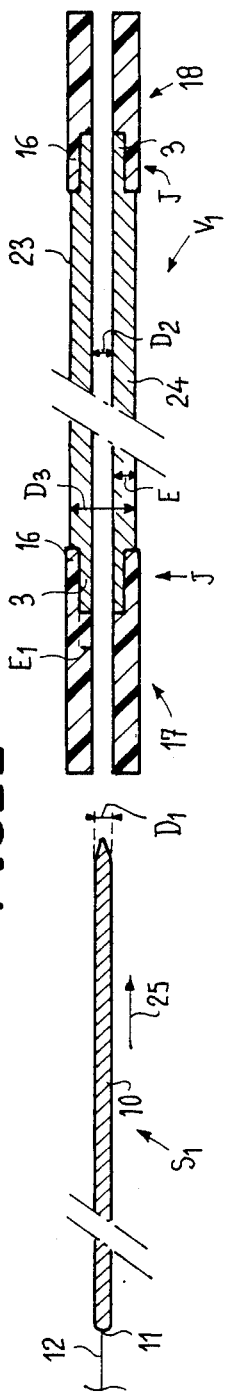
FIG_2

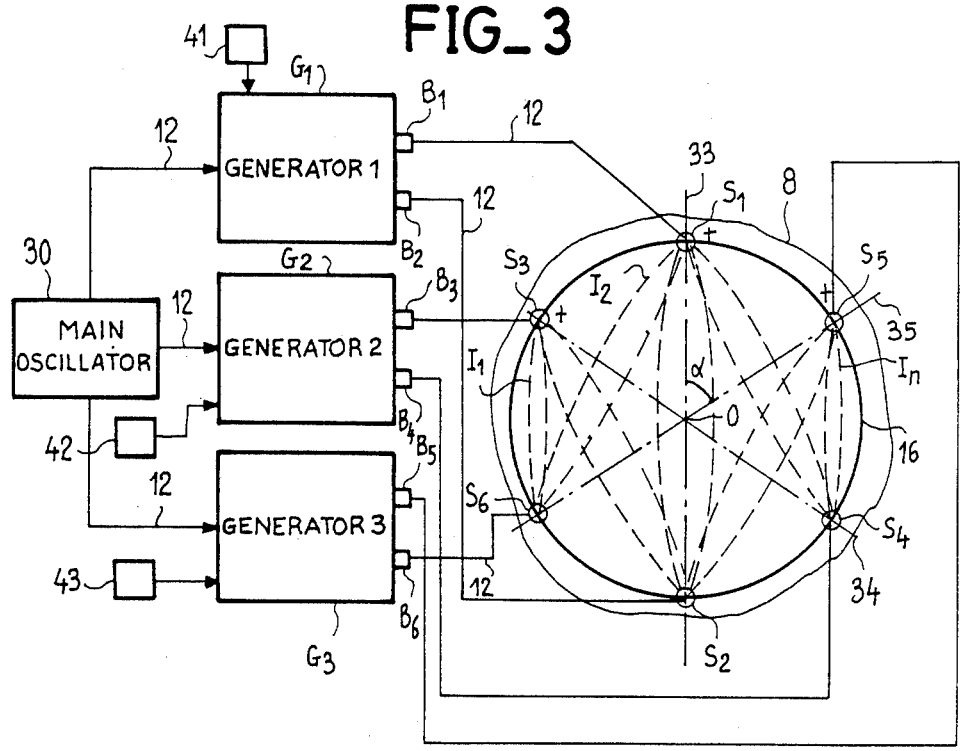
FIG_3
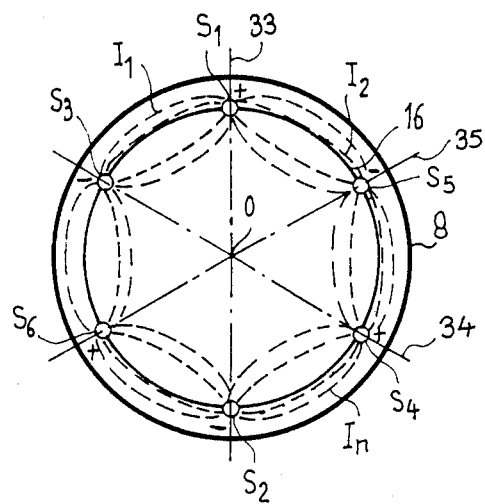
FIG_4

DEVICE FOR TREATMENT THROUGH HYPERTHERMIA

BACKGROUND OF THE INVENTION

1. Field of the Invention

The invention concerns a device for treatment through hyperthermia, allowing to heat a diseased area of a patient through dissipation of an electrical energy applied according to an electrical field through of unipolar electrodes disposed adjacent to the diseased area or within said area. The invention is of particular interest in that it allows to considerably reduce the effects traumatizing for the patient, produced by using such treatments.

2. Summary of the Prior Art

Hyperthermia is a known process, which consists in heating living biological tissues to temperatures substantially higher than their normal temperature, and which is utilized in the treatment of various illnesses and especially in cancerotherapy. In the example of this latter application, it is desirable to heat the tissues to be treated to temperatures of about 44° C. to 45° C., while avoiding, as much as possible any substantially increase in temperature of the healthy surrounding tissues.

This condition raises a problem which resides in the correct localization of the heated area. In certain configurations which the diseased tissues can present, this correct localization of the heating is impossible to obtain with electrodes situated outside the patient's body. Therefore, in numerous cases, treatment by hyperthermia is carried out through using electrodes directly implanted in or around the area to be treated, so as to more closely confine the area heated.

Such probes can be either of the bipolar or the unipolar type. In the case of bipolar probes, the high frequency electric energy supplied by a generator, in the form of a voltage, can be applied to a single probe of this type, to heat the area in which it is implanted. In the case of unipolar probes, the high or average frequency voltage supplied by the generator is applied to two separate unipolar probes, each of these two probes being connected to one of the output poles of the generator, the heated zone thus being mainly established between two unipolar probes of the type that can be implanted.

The implantation of a bipolar or unipolar probe in a diseased area represents for a patient an operation that can be accompanied by acute pain, and which is particularly traumatizing for treatments by hyperthermia for a given zone to be treated, must generally be repeated at variable frequencies and over periods of time comprised between several days and several tens of days.

Another painful or at least disagreeable effect for the patient is associated with the particular sensibility of cutaneous tissues to high temperatures. In fact, experiments have shown that it is not generally possible for the patient's comfort, to maintain, without an anaesthetic, a temperature of about 43° with respect to the skin during periods of about 1 hour.

Another source of considerable inconvenience for the patient, during treatment, is associated to the mechanical rigidity of the probes, especially unipolar probes. These latter are generally constituted by metal needles, that are relatively rigid and which can, even after they have been placed in position, constitute a source of pain or ache more particularly while passing through the skin.

A general object of the present invention is to produce a structure for implanting unipolar or bipolar probes allowing to reduce as such as possible the disagreeable effects to which the patient is subjected.

More specifically, one of the objects of the invention is to suppress the disagreeable effects caused by repeatedly implanting the probes.

Another object of the invention is to suppress the heating of the skin during treatment by hyperthermia of the cutaneous tissues.

Similarly, another object of the invention is to suppress or attenuate the disagreeable effects to the skin caused by the rigidity of the probes.

It is to be noted furthermore that during treatment, certain tissues of the area to be treated can undergo different rises in temperature, this being able to lead during treatment to modifying the implantation of the probes. Therefore, one of the objects of the invention is also to allow to modify the configuration of the heated area, without requiring that the implantation of the probes be modified.

SUMMARY OF THE INVENTION

According to the invention, a device for treatment through hyperthermia is provided, which comprises, at least one generator supplying an alternating electric power, the said electric power being applied, according to an electric field, to an area to be treated of a patient through unipolar electrodes connected to the said generator, at least one of the said unipolar electrodes being an implantable unipolar probe, said device comprising furthermore at least one vector tube intended to be implanted permanently in the area to be treated by crossing through the patient's skin and containing the said unipolar probe during a hyperthermia session the said vector tube comprising at least one tubular end formed of an insulating material and extended by a metallic tube, the said metallic tube being adapted to contain at least partially the said unipolar probe and to be in contact with the said area to be treated, and the said tubular end being intended to be situated at the level of the skin, the said unipolar probe being introduced through the said tubular end into the said metallic tube with which the said unipolar probe is in electrical contact.

By the expression "placed permanently" is meant with respect to the vector tube a period of time, for example, several days, during which time several hyperthermia sessions are scheduled for which the placing in position of the electrodes or unipolar probes is carried out by their introduction into a vector tube.

It is to be noted that one considerable advantage provided by the invention is to enable to associate easily a treatment by radiotherapy to a hyperthermia treatment; the save vector tubes can be used:

a—to introduce the radioactive needles (polonium or the like) for the radiotherapy sessions;

b—to introduce unipolar probes, for the hyperthermia sessions.

BRIEF DESCRIPTION OF THE DRAWINGS

The invention will become more apparent from the following description, given by way of non-limitative illustration, with reference to the four appended drawings in which:

FIG. 1 illustrates the implanting of unipolar probes in a zone to be treated, with a first version of a device for treatment by hyperthermia according to the invention;

FIG. 2 shows details of a vector tube intended according to the present invention to contain a unipolar probe;

FIG. 3 schematically shows a second version, with several generators, of a treatment device according to the invention allowing easily to modify the distribution of the currents in the zone to be treated;

FIG. 4 schematically illustrates a distribution of the currents as modified with respect to FIG. 3.

DETAILED DESCRIPTION OF THE INVENTION

FIG. 1 illustrates a hyperthermia treatment device 1 according to the invention, and an example of implantation of unipolar probes S1, S2.

The treatment device comprises a generator G1 of the type operating at average or high frequency (in the range of 100 KHz to several MHz), and average power (in the range of several tens of Watt to several hundreds of Watt). The generator G1 supplies, across a first and a second output terminal 4, 5 an alternating electric energy intended to be dissipated within the body 6 (partially represented) of a patient, in order to raise the temperature of an area 8 to be treated by hyperthermia. The electric energy supplied by the generator G1, in the form of a voltage (not represented) for example, is applied to the unipolar probes S1, S2, the first unipolar probe S1 being for this purpose connected to the first output terminal 4 and the second unipolar probe S2 being connected to the second output terminal 5. In the non-limitative example described, the unipolar probes S1, S2 are both of the implantable type, i.e. constituted by a metallic needle 10, one end 11 of which is connected to a conventional electrically conductive wire 12 through which they are connected to the generator G1; but it is also known in the prior art, and this can also be applied when carrying out the invention, to use a single implantable probe S1, S2 of the unipolar type cooperating with a unipolar electrode (not represented) adapted to be placed inside the patient's body 6.

According to the prior art, as explained in the preamble of the present description, implantable unipolar probes are directly implanted in the tissues to be treated at each hyperthermia session, contrary to the possibilities offered by the present invention.

In fact, according to the present invention, the treatment device 1 furthermore comprises vector tube V1, V2 provided so as to be implanted in the zone 8 to be treated or adjacent thereto, as represented in the non-limitative example of FIG. 1, and to be left there permanently, i.e. over a period of time during which several sessions of treatment by hyperthermia are performed. The vector tubes V1, V2 are adapted to receive, during each treatment session, a unipolar probe S1, S2 introduce into a vector tube V1, V2 through a first or a second end 17, 18 of this latter, at least one of these ends 17, 18 having to be placed for this purpose outside the patient's body 6, i.e. protruding with respect to the patient's skin 20.

FIG. 2 shows more clearly, by way of non-limitative example, a vector tube V1 and a unipolar probe S1. The first and second ends 17, 18 of the vector tube V1, at least one of which is necessary, are produced, according to one characteristic of the invention, from an electrically insulating material, and according to another characteristic of the invention, this material should furthermore be flexible, these characteristics both contributing to the comfort of the patient as will be described hereinbelow. These conditions are met by using materials, such as for example a polyamide known under the trademark "Nylon ®" or a polytetrafluoroethylene known under the name of TEFLON ®. The first tubular end 17 is extended by a metallic tube 23, communicating with the tubular end 17, so that a unipolar probe S1 can be introduced in the direction shown by the first arrow 25, for example, up to within the metallic tube 23. In the non-limitative example described, the metallic needle 10 of the unipolar probe S1 has a diameter DI substantially smaller than the internal diameter D2 of the metallic tube 23; this allows to ensure in a simple way an electrical contact between the metallic needle 10 and the metallic tube 23 when the needle is introduced at least partially into this latter. Supposing that the needle 10 has in a conventional way a diameter D1 of about 0.8 mm, and that the internal diameter D2 of the metallic tube 23 is about 0.9 to 1 mm for example, in order to allow the passage of the needle 10 and to ensure the electrical contact and that, on the other hand, the wall 24 of the metallic tube 23 comprises a thickness E of about 0.1 to 0.15 mm, the external diameter D2 of the metallic tube 23 will be about 1.1 to 1.2 mm. The assembly of the metallic tube 23 and the tubular ends 17, 18, can be carried out by those skilled in the art in different ways, as, for example, represented in FIG. 2; as shown there, the metallic tube 23 comprises next to its Junction J with the tubular ends 17, 18 an end part 3 where the wall 24 has a smaller thickness E1, so that the tubular end 17 can be sunk on this end part 3 without creating any significant overthickness with respect to the external diameter D3; the end part 3 thus comprises an electrically insulating oversheathing 16.

The implantation of the vector tube V1 in the area 8 to be treated can be carried out by using a hollow needle (not represented) of the type called vector cradle, for example, the use of which in the medical field is current, especially for the implantation of various probes in living tissue; said vector cradle is also described in French patent published under No. 2 421 628. The vector tube V1 can be placed in the vector cradle, which is thereafter introduced at the desired site into the zone 8 to be treated; the vector cradle is thereafter withdrawn with care by causing to it to slide on the vector tube V1 which remains in place.

Referring again to FIG. 1, the vector tubes V1, V2 being placed in position each unipolar probe S1, S2 is introduced into a vector tube V1, V2. The unipolar probe S1, S2 being connected to the generator G1, and said generator operating, an electrical field represented on FIG. 1 by field lines $I_1, I_2 \ldots I_n$ is established between the unipolar probes S1, S2 through the intermediary of the vector V1, V2 in order to produce a rise in temperature of the area to be treated 8 subjected to the electrical field. One advantage of this disposition resides in the fact that it allows to confer upon vector tubes V1, V2 active lengths respectively L1, L2 between which is established an electrical field, independently from the lengths L3 of the unipolar probes S1, S2, this allowing to confine more accurately the zone 8 subjected to the electrical field. In fact for frequencies lower than several MHz, thicknesses of insulating materials of about 0.10 mm are sufficient to prevent the establishment of the electric current. In the non-limitative example described, the active lengths L1, L2 correspond to the length of the metallic tubes 23 exposed, i.e. not sheathed by the tubular ends 17, 18 of insulating material. This allows in particular to confer active lengths L1, L2 of possibly different dimensions, compatible with the geometry of the zone 8 to be treated, while using unipolar probes S1, S2 having metallic needles 10 of identical lengths L3.

The tubular ends 17, 18 ensure furthermore protection with respect to the skin 20, which is particularly sensitive to rises in temperature. Thus, for example, in the case where on unipolar probe, the second unipolar probe S2 for example is situated at the level of the skin 20, not being for example entirely fitted into the second vector tube V2; the end 11 of the needle 10 connected to the wire 12 thus being situated outside the patient's body 6, at a location 11' marked for example, the presence of the tubular end 17 prevents the establishment of the electrical field at the level of the skin 20 and thus prevents the burning sensations felt by the patient in such a case. This possibility of withdrawal of a unipolar probe S1, S2 is the more important as it allows to release in the vector tube V1, V2 a zone Z opposite to the first end 17, into which can be introduced through the second end 18, a needle made of a radioactive material (not represented) of a conventional type. This allows to carry out simultaneously a treatment by hyperthermia and a treatment by radiotherapy.

Another very important advantage for the patient's comfort is contributed by the flexibility of the tubular ends 17, 18 which allows relative movements thereof with respect to a longitudinal axis 28 of the IO unipolar probes S1, S2 this flexibility allowing them to follow the movements of the skin due for example to slight movements of the patient, thus allowing to avoid that the patient experiences painful sensations.

In the non-limitative example represented in FIG. 1, two vector tubes V1, V2 have been represented but a greater number n of these vector tubes V1, V2 ... Vn can be implanted permanently in the case, for example, where a greater number of unipolar probes S1, S2 are used with for example several generators (not represented on FIG. 1) or again in the case where the practitioner desires to modify the heating configuration of a treated zone 8. Such a modification can be desirable from one hyperthermia session to another, or even during the same session, in the case for example where the tissues (not represented) of one zone to be treated 8 have different sensitivies to the electrical field.

FIG. 3 schematically illustrates a second version of the treatment device 1 according to the invention, which allows to carry out modifications of the heated area such as mentioned herein-above, without requiring modification of the implantation position of the vector tubes V1, V2 ... already implanted (not represented on FIG. 5 for enhanced clarity). It is to be noted that this version of the invention can also be applied in the case of a conventional utilization of implantable unipolar probes, i.e. without vector tubes V1, V2 ... V3.

In this second version, the treatment device 1 should comprise, further to the first generator G1, at least one supplementary generator G2, i.e. at least two frequency synchronized generators G1, G2.

Therefore, in the non-limitative example described, the treatment device comprises, in addition to the first generator G1, a second and a third generator G1 substantially of the same type as the first generator G1, a number N of generators, higher than 3 can also be used. In the non-limitative example described, the treatment device 1 comprises furthermore a main oscillator 30 connected by connections 31 to each of the generators G1, G2, G3 in order that these latter operate at a single frequency F1 and according to a single phase.

The area 8 to be treated is represented on FIG. 3 by a cross-sectional view in a plane perpendicular to the longitudinal axis 28 shown in FIG. 1. In the example described, six unipolar probes S1, S2 ... S6 are either implanted directly in the area 8 to be treated, or each is placed as in the previous example, in a previously implanted vector tube, the unipolar probes S1, ... S6 being shown in cross-section, they are represented on FIG. 3 by circles. In the non-limitative example described, the unipolar probes S1, ... S6 are disposed in an area 8 to be treated substantially on a circle 16 having a centre 0, through which pass three axes 33, 34, 35 forming between them an angle alpha of about 30°; two unipolar probes S1, ... S6 connected to the save generator G1, G2, G3 in the non-limitative example described, disposed on a single axis 33, 34, 35 but opposite with respect to the center 0. Each of the probes S1, ... S6 is connected by an electric conductor 12 to one of the output terminals B1, B2 ... B6 of a generator GI, G2, G3:

the first and the second probes S1, S2 disposed on the first axis 33 are connected respectively to the first and the second terminal B1, B2 of the first generator G1;

the third and fourth probes S3, S4 disposed on the second axis 34, are connected respectively to a third and fourth output terminal B3, B4 of the second generator G2;

the fifth and sixth probes S5, S6 disposed on the third axis 35, are connected respectively to a fifth and a sixth terminal B5, B6 of the third generator G3.

The three generators G1, G2, G3 operate at an idetnical frequency F1, and thus, by determining the polarities +,— (for a given instant) of the output terminals B1, B2 and B3, B4 and B5, B6 corresponding to each of the enerators G1, G2, G3, it is possible to place unipolar probes S1 to S6 corresponding to a desired position in the area 8 to be treated, such as for example shown on FIG. 3, so as to establish the electrical field between these unipolar probes S1 to S6 according to a desired arrangement; this positioning of the probes can be carried out through direct implantation or by placing each probe in a vector tube as explained herein-above.

Supposing that the first, third and fifth output terminals B1, B3, B5 have a positive polarity +, the second, fourth and sixth output terminals B2, B4, B6 will have a negative polarity —, these +,— polarities appearing respectively at the unipolar probes S1, S3, S5 and S2, S4, S6.

The electrical field represented by the field lines $I_1$ to $I_n$ will be in these conditions established in the whole of the area 8 to be treated.

As mentioned herein-above, it can be desirable to modify the distribution of the electrical field, i.e. the configuration of the heated area. This is possible according to the invention, without causing any supplementary discomfort to the patient, either by substituting the unipolar probes S1, ... S6 between one another, with respect to the vector tubes, in the case where the latter are used, or by modifying the respective +,— polarity of the probes S1, to S6 by acting on the generators G1, G2, G3 as well in the case where the unipolar probes S1 to S6 are directly implanted in the area 8 to be treated, as in the case where they are disposed in the vector tubes. For this purpose, each of the generators G1, G2, G3 comprises an inverter device respectively 41, 42, 43 allowing to invert the polarity between two output terminals B1, B2 and B3, B4 and B5, B6 of any single generator G1, G2, G3. The commutation devices 41, 42, 43 can consist of conventional commutating means allowing for example for the first generator G1 to invert the connections (not represented) established between the output terminals B1, B2 and the amplifiers (not represented) conventionally provided on each generator G1, G2, G3. Such an inversion of polarities can be carried out in different ways, all of which are within the scope of those skilled in the art, and can also consists in an inversion of the conducting wires 12 connected to the output terminals B1, B2.

It is also possible through modifying the polarity of the probes S1 to S6, to obtain modification of the distribution of the electrical field, as form example represented in FIG. 4.

FIG. 4 represents the area 8 to be treated according to a view analog to that of FIG. 3, i.e. taken in a plane perpendicular to the longitudinal axis 28 shown on FIG. 1, the unipolar probes S1 to S6 occupy the same position as FIG. 3, but comprise different +,− polarities, so that these polarities are successively positive +and negative −. The electrical field represented by the field lines $I_1, \ldots I_n$ established between the adjacent probes in +,− polarities thus corresponds substantially to a circular distribution around the circumference of circle 16, i.e. around the center 0 which in this configuration is not subjected to the electrical field.

Other heating configurations of the area 8 to be treated can be obtained, by modifying either the distribution of the probes S1, . . . S6 in the vector tubes V1, V2 . . . or by modifying the positive + or negative − polarity conferred upon each of the probes.

The present description constitutes a non-limitative example of a treatment device 1 by hyperthermia according to the invention, in which n tubes vector V1, V2 . . . Vn adapted to be implanted permanently allow to suppress the causes of the discomfort felt by the patient with treatment appliances according to the prior art; a treatment device 1 according to the invention allows furthermore to carry out an appropriate heating of the area 8 to be treated, with much more flexibility than in the prior art.

What is claimed is:

1. A device for treatment through hyperthermia comprising:
    at least one generator;
    at least two unipolar electrodes connected to said generator, said generator supplying an alternating electric energy, the said electric energy being applied, according to an electric field, to an area to be treated of a patient by means of said unipolar electrodes connected to the said generator, at least one of the said unipolar electrodes being an implantable unipolar probe, said device further comprising at least one vector tube adapted to be implanted permanently in the area to be treated by crossing through the patient's skin and to contain one of the said unipolar probes during a hyperthermia session the said vector tube comprising at least one tubular end formed of an insulating material and extended by a metallic tube, the said metallic tube being adapted to contain at least partially the said unipolar probe and to be in contact with the said area to be treated, and the said tubular end being adapted to be situated at the level of the skin, the said unipolar probe being introduced through the said tubular end into the said metallic tube with which the said unipolar probe is in electrical contact.

2. A treatment device according to claim 1, wherein at least one said tubular end is made of a flexible material.

3. A treatment device according to claim 1, wherein at least one said tubular end is made of polytetrafluoroethylene.

4. A treatment device according to claim 1, wherein the said vector tube has an active length defined by the said metallic tube.

5. A treatment device according to claim 4, wherein said active length is independent from the length of the said unipolar probe.

6. A treatment device according to claim 5, wherein the said active length is limited by at least one electrically insulating sheath provided on the said metallic tube.

7. A treatment device according to claim 1, wherein there are two probes and said device further comprising at least one second generator frequency synchronized with the first generator and connected to a third and a fourth unipolar probe cooperating with said two probes in order to heat the said area to be treated.

8. A treatment device according to claim 7, comprising means for modifying the distribution of the said electrical field without modifying the implantation of the said probes.

9. A treatment device according to claim 8, wherein at least one of the said generators comprises commutating means to invert the +,− polarity applied to the two unipolar probes to which it is connected, in order to modify the distribution of the electrical field to which is subjected said area to be treated.

10. A treatment device according to claim 9, further comprising a main oscillator connected to the said first and second generators in order to cause them to operate at the same frequency.

* * * * *